(12) United States Patent
Chang et al.

(10) Patent No.: US 12,145,964 B2
(45) Date of Patent: Nov. 19, 2024

(54) THIOPHOSPHORODICHLORIDATE REAGENTS FOR CHEMOSELECTIVE HISTIDINE BIOCONJUGATION

(71) Applicant: The Regents of the University of California, Oakland, CA (US)

(72) Inventors: Christopher J. Chang, Berkeley, CA (US); Shang Jia, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 896 days.

(21) Appl. No.: 17/207,609

(22) Filed: Mar. 20, 2021

(65) Prior Publication Data

US 2021/0230215 A1 Jul. 29, 2021

Related U.S. Application Data

(63) Continuation of application No. PCT/US2019/056018, filed on Oct. 13, 2019.

(60) Provisional application No. 62/749,670, filed on Oct. 23, 2018.

(51) Int. Cl.
*C07K 1/13* (2006.01)
*C07K 1/113* (2006.01)
*C07K 14/00* (2006.01)

(52) U.S. Cl.
CPC .............. *C07K 1/13* (2013.01); *C07K 1/113* (2013.01); *C07K 14/00* (2013.01); *C07K 2319/21* (2013.01)

(58) Field of Classification Search
CPC .......... C07K 1/13; C07K 1/113; C07K 14/00; C07K 2319/21
See application file for complete search history.

(56) References Cited

PUBLICATIONS

Delley, Richard J. Kinetic Studies of the Hydrolyses and Aminolyses of Phosphorus (V) Chlorides and proton transfer at carbon. Thesis, Degree of Doctor of Philosophy, Durham University 2012, pp. 1-238. (Year: 2012).*

Nyquist et al. Vibrational spectroscopic study of H-C C-H2-O-P(S)Cl2; Abstract, Journal of Molecular Structure 1968, vol. 2, Issue 6. (Year: 1968).*

* cited by examiner

*Primary Examiner* — Shafiqul Haq
(74) *Attorney, Agent, or Firm* — Richard Aron Osman (57) ABSTRACT

Proteins are labeled by contacting the protein with a thiophosphorodichloridate reagent under conditions to effect chemoselective histidine conjugation.

15 Claims, 4 Drawing Sheets

THIOPHOSPHORODICHLORIDATE REAGENTS FOR CHEMOSELECTIVE HISTIDINE BIOCONJUGATION

This invention was made with government support under Grant Number ES028096 awarded by the National Institutes of Health. The government has certain rights in the invention.

INTRODUCTION

Site-selective bioconjugation chemistry offers a versatile strategy to probe and expand the function of proteins.[1-5] The most common and robust chemoselective and regioselective protein bioconjugation strategies have focused on functionalization of cysteine thiol[6-9] and lysine amine[10-12] sites and related nucleophilic hydroxyl[13,14] and carboxyl[15] side chains. More recent advances in protein bioconjugation technologies have targeted access to less nucleophilic amino acids,[16] including tyrosine,[17-19] tryptophan[20,21] and methionine.[22] In contrast, selective modification of histidine, which is commonly found in enzyme active sites and metal-binding sites,[23,24] remains underexplored. Because the imidazole side chain of histidine is a good metal ligand, metal coordination can enable protein modification through metal-directed covalent labeling proximal to the histidine group[25,26] or direct non-covalent metal-histidine complexation,[27-31] the latter of which can be labile under biological contexts or mass spectrometry conditions. On the other hand, histidine is a useful catalytic component owing to its ability to serve as both a good nucleophile and leaving group, but this character also makes it difficult to form stable bonds with the imidazole side chain through electrophilic functionalization. Indeed, selected epoxides are histidine-reactive but typically require harsh reaction conditions such as high temperatures and/or strong bases[32,33] or an affinity-directed ligand.[34,35]. As such, selective and direct covalent labeling of histidine remains a challenge.

Inspired by observations of reversible histidine phosphorylation as an emerging post-translational modification in prokaryotes and eukaryotes and elegant studies to probe its biological functions, we developed and disclose here a histidine-selective bioconjugation method that mimics this type of chemistry.

SUMMARY OF THE INVENTION

We disclose a strategy for histidine modification using thiophosphorodichloridate reagents that mimic post-translational histidine phosphorylation, enabling fast and selective labeling of protein histidines under mild conditions where various payloads can be introduced via copper-assisted alkyne-azide cycloaddition (CuAAC) chemistry. We establish that these reagents are particularly effective at covalent modification of His-tags, which are common motifs to facilitate protein purification, as illustrated by selective attachment of polyarginine cargoes to enhance the e uptake of proteins into living cells. This technology provides numerous applications, including probing and enhancing protein function using histidine-directed chemistry. For example, our bioconjugation strategy can be used to generate bioconjugates on polyhistidine tags commonly found in recombinant proteins, as well as on single histidine residues. These bioconjugates, such as antibody-drug conjugates, immobilized antibodies or enzymes, PEGylated proteins and so on, can be used in pharmaceutics and diagnostics. The invention provides our conjugation method and related compositions and kits.

In an aspect the invention provides a method of labeling a protein comprising reacting the protein with a thiophosphorodichloridate reagent under conditions to effect chemoselective histidine conjugation and form a resultant conjugate of the protein and the reagent.

In embodiments:
the method further comprises introducing on the reagent a molecular payload via chemistry selected from copper-assisted alkyne-azide cycloaddition (CuAAC) chemistry, strain-promoted alkyne-azide cycloaddition (SPAAC), oximes and hydrazones formation, tetrazine ligation and so on;

the reagent comprises a functional group configured for the selected conjugation chemistry, such as alkyne or azide groups, or any other handle operative in the selected conjugation chemistry, such as thiophosphoro alkyne dichloridate (TPAC);

the payload is a small molecule pharmaceutical, a DNA, an RNA, a lipid, a sugar, a polypeptide, a protein, a detectable label, and so on, such as a fluorescent label (e.g. Cy3) or affinity tag (e.e. desthiobiotin);

the conjugate is of general formula:

wherein R1 is a polypeptide (e.g. peptide, enzyme, an antigenic protein, a chemokine, a cytokine, a cellular receptor, a cellular receptor ligand, or an antibody or active fragment thereof), R2 is a payload moiety (e.g. small molecule pharmaceutical, a DNA, an RNA, a lipid, a sugar, a polypeptide, a protein, a detectable label and so on), and L is an optional linker compatible with the reaction conditions and required functionalities;

the protein comprises a polyhistidine tag and the method effects covalent modification of the tag; and/or the conjugation is bioconjugation, functional in a living cell.

In another aspect the invention provides a composition comprising or a compound that is a conjugate of general formula:

wherein R1 is a polypeptide (e.g. peptide, enzyme, an antigenic protein, a chemokine, a cytokine, a cellular receptor, a cellular receptor ligand, or an antibody or active fragment thereof), F is a functional group configured for the selected conjugation chemistry, such as alkyne or azide groups, or any other handle operative in the selected conjugation chemistry, such as thiophosphoro alkyne dichloridate (TPAC).

In embodiments:
the composition further comprises an unconjugated thiophosphorodichloridate reagent, and/or an unconjugated R1 polypeptide.

In an aspect the invention provides a composition comprising a conjugate of general formula:

wherein R1 is a polypeptide (e.g. peptide, enzyme, an antigenic protein, a chemokine, a cytokine, a cellular receptor, a cellular receptor ligand, or an antibody or active fragment thereof), R2 is a payload moiety (e.g. small molecule pharmaceutical, a DNA, an RNA, a lipid, a sugar, a polypeptide, a protein, a detectable label and so on), and L is an optional linker compatible with the reaction conditions and required functionalities.

In embodiments the composition further comprises an unconjugated thiophosphorodichloridate reagent, an unconjugated R1 polypeptide, and/or an unconjugated R2 payload molecule.

The invention encompasses all combination of the particular embodiments recited herein, as if each combination had been laboriously recited.

BRIEF DESCRIPTION OF THE DRAWINGS

FIGS. 1A-1D. Labelling of histidine with phosphorus electrophiles.

FIGS. 2A-2F. Model protein tagging with TPAC. FIG. 2D: Calmodulin, FIG. 2E: myoglobin and FIG. 2F: lysozyme are also labelled by TPAC as shown by their deconvoluted mass spectra. TPAC-modified calmodulin: expected mass 16924 Da, found 16924 Da; single, double and triple TPAC modified myoglobin: expected mass 17085, 17219 and 17353 Da, found 17085, 17218 and 17352 Da; single and double TPAC modified lysozyme: expected mass 14439, 14573 Da, found 14438, 14572 Da. Their crystal structures (PDB 2o60, 1bje and 193I) are shown as insets highlighting the major modified histidines. Conditions: 20 µM protein, 2 mM TPAC in 25 mM HEPES with pH 8.5, room temperature, 1 h unless otherwise noted.

FIGS. 3A-3B. Protein bioconjugation with TPAC.

FIGS. 4A-4D. Functionalization of His-tag on GFP to enable protein delivery.

DESCRIPTION OF PARTICULAR
EMBODIMENTS OF THE INVENTION

Unless contraindicated or noted otherwise, in these descriptions and throughout this specification, the terms "a" and "an" mean one or more, the term "or" means and/or. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Thiophosphorodichloridate Reagents for Chemoselective Histidine Bioconjugation

Site-selective bioconjugation to native protein residues is a powerful tool for protein functionalization, with cysteine and lysine side chains being the most common points for attachment owing to their high nucleophilicity. We disclose strategy for histidine modification using thiophosphorodichloridate reagents that mimic post-translational histidine phosphorylation, enabling fast and selective labeling of protein histidines under mild conditions where various payloads can be introduced via copper-assisted alkyne-azide cycloaddition (CuAAC) chemistry. We establish that these reagents are effective at covalent modification of His-tags, which are common motifs to facilitate protein purification, as illustrated by selective attachment of polyarginine cargoes to enhance the uptake of proteins into living cells.

Figure 1A:
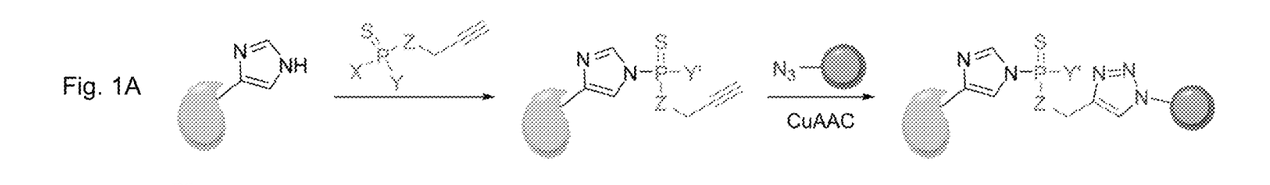
FIG. 1A: Scheme of histidine labeling and the following click reaction for bioconjugation. X, Y=Cl, OH, OMe or $NH_2$, Z=O, NH or S.
Figure 1B:
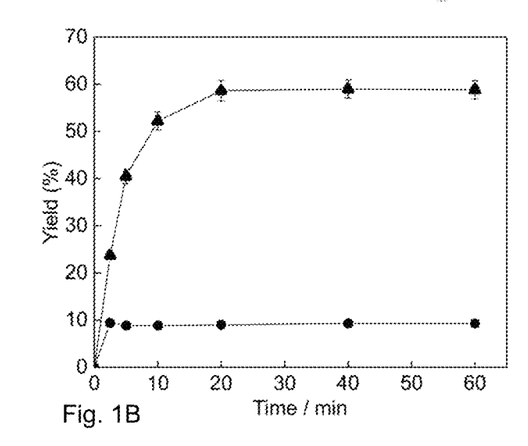
FIG. 1B: Kinetics of reaction between TPAC and Fmoc-His-OH. Triangle: pH 8.5. Circle: pH 7.5.
Figure 1C:
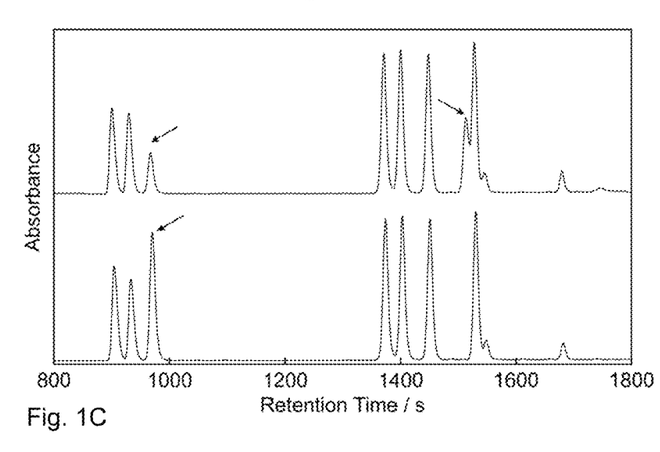
FIG. 1C: HPLC chromatograph showing the reaction between TPAC and Fmoc-His-OH in the presence of competing Fmoc-protected amino acids. Top: reaction mixture of TPAC and amino acids. Bottom: amino acids mixture; left to right: Fmoc-Lys, Fmoc-Arg, Fmoc-His, Fmoc-Ser, Fmoc-Glu, Fmoc-Thr and Fmoc-Tyr. Arrows point to Fmoc-His-OH (left) and TPAC-labelled Fmoc-His-OH (right, ESI-MS m/z expected 512.1, found 512.2 for $M+H^+$).
Figure 1D:
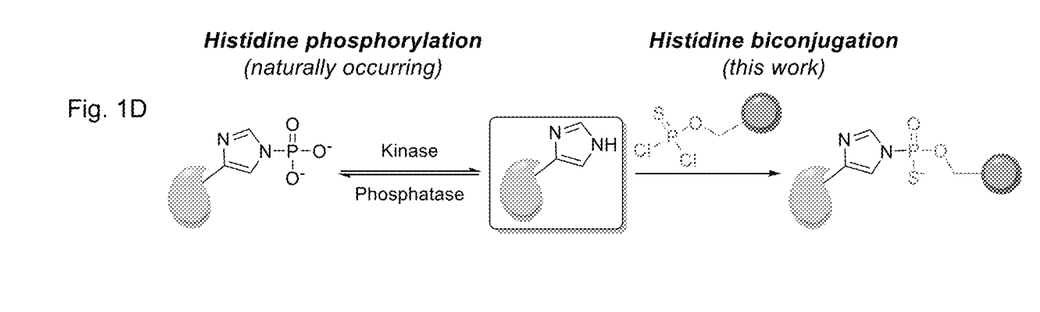
FIG. 1D: Histidine phosphorylation and histidine bioconjugation.

Design and synthesis. Inspired by observations of reversible histidine phosphorylation as an emerging post-translational modification in prokaryotes and eukaryotes and elegant studies to probe its biological functions,[36-39] we sought to develop a histidine-selective bioconjugation method that mimics this type of chemistry (FIG. 1A). We turned our attention to phosphorus-based electrophiles, based on precedent that potassium phosphoramidate can selectively phosphorylate histidine[40,41] and that thiophosphoryl chloride and potassium thiophosphoramidate can generate thiophosphohistidine analogs with improved aqueous stability.[42-44] To this end, we synthesized a series of phosphorus electrophiles with varying reactivity as suggested by their different synthesis and handling methods (Scheme 1). We first tested thiophosphoramidate 1 combining a phosphosulfide moiety for histidine labeling and an alkyne group for further functionalization, but this compound did not show an observable reaction with Fmoc-His-OH in buffered aqueous solution (Scheme 2). We then tested compound 2, where we hypothesized that installation of chloride as a better leaving group might enhance reactivity. Indeed, thiophosphochloride 2 did show appreciable labeling of Fmoc-His-OH, but the resulting product underwent significant hydrolysis back to the unmodified histidine over prolonged incubation at neutral pH (Scheme 2), presumably due to the high acidity of the thiophosphoric acid diester as a leaving group.[45] To prevent this observed hydrolysis, we further replaced the methoxy group with another chloride that eventually hydrolyzes to the corresponding hydroxy congener to introduce a negative charge, akin to stable phosphate diester linkers found in nucleotides. The resulting compound 4, termed thiophosphoro alkyne dichloridate (TPAC), gave higher conversion to product that is resistant to hydrolysis (Scheme 1, Table 1). The thiophosphorus electrophiles 2 and TPAC are superior histidine labeling reagents compared to their oxygen counterparts 3 and 5, presumably owing to the greater stabilization provided by the less electronegative sulfur. The thiophosphodichloridate can be functionalized with other clickable handles such as azide 8 and sterically hindered alkyne 9 that show comparable reactivity. Further characterization using TPAC as a representative thiophosphodichloridate reagents shows optimal histidine labeling at more basic pH values, affording a 60% yield of bioconjugate within twenty minutes at pH 8.5 (FIG. 1B). The short observed reaction time for TPAC-mediated histidine labeling is primarily controlled by the fast hydrolysis of TPAC itself, which is advantageous since the reaction does not require quenching of residual TPAC to halt its reactivity and the reagent can thus be used in excess. Moreover, the thiophospho-histidine product shows reasonable stability under various conditions including high temperature, acidic, basic, reducing and alkylating environments (Table 1). Most importantly, TPAC exhibits high selectivity for histidine, showing negligible reactivity on other nucleophilic amino acids (FIG. 1C). The results collectively identify TPAC as a promising candidate for chemoselective bioconjugation to histidine.

Figure 2A:
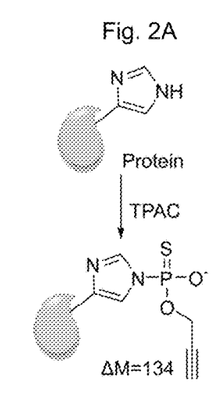
FIG. 2A: Structure and mass difference of the histidine modification by TPAC.
Figures 2B, 2C:
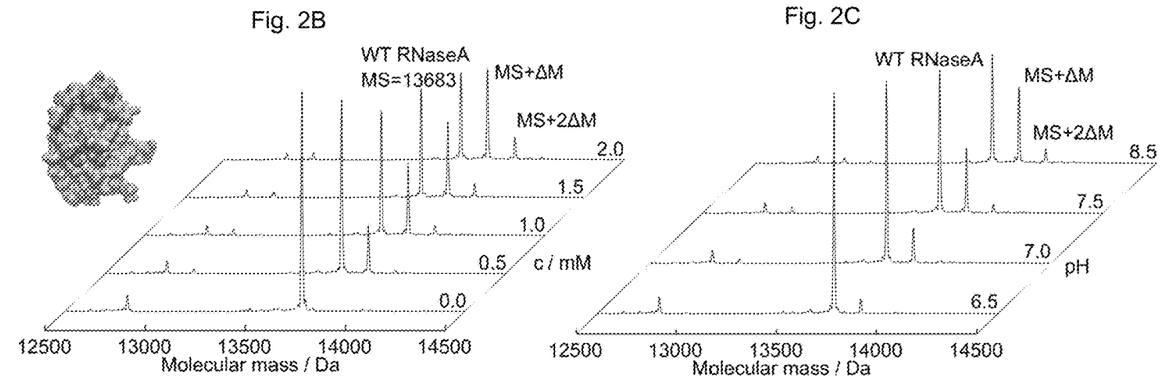
FIG. 2B: Deconvoluted mass spectra showing ribonuclease A labelled by TPAC with concentration ranging from 0 to 2 mM. Single and double TPAC modified RNaseA: expected mass 13817, 13951 Da, found 13816, 13950 Da. Its crystal structure (PDB 1bel) is shown in the inset highlighting its major modified histidine.
FIG. 2C: Deconvoluted mass spectra showing ribonuclease A labelled with 1.5 mM of TPAC with different buffered pH.

TPAC bioconjugation on model proteins. With these results in hand, we moved on to test TPAC labeling of histidine on intact protein substrates. We used ribonuclease A as a model protein and analyzed bioconjugation reactions by mass spectrometry. The TPAC labeling is dose-dependent, generating ca. 45% singly-modified protein and 11% doubly-modified protein at pH 8.5 (FIG. 2B). Similar to what was observed in small-molecule amino acid models, the TPAC-ribonuclease A coupling reaction was more effective at slightly basic conditions compared to neutral pH (FIG. 2C). We further performed LC-MS/MS of the digested protein to analyze the site of modification. Similar to other phosphopeptides, the TPAC modification undergoes significant neutral loss in collision-induce dissociation (CID), but the fragment peaks are sufficient for identifying the site of modification. We also used electron-transfer dissociation (ETD) on peptides with ambiguous modification sites for supplementary information. Interestingly, the LC-MS/MS of the digested protein indicates that the reaction occurs primarily on H48, a surface-exposed histidine rather than histidines at the catalytic center (H12 and H119). In addition, two other histidine sites, on at the active site (H119) and one that is not (H105), are also modified to less extent, as shown qualitatively by extracted precursor ion chromatogram. The data are also in line with the negligible loss of activity of ribonuclease A after TPAC treatment.

Figure 2D:
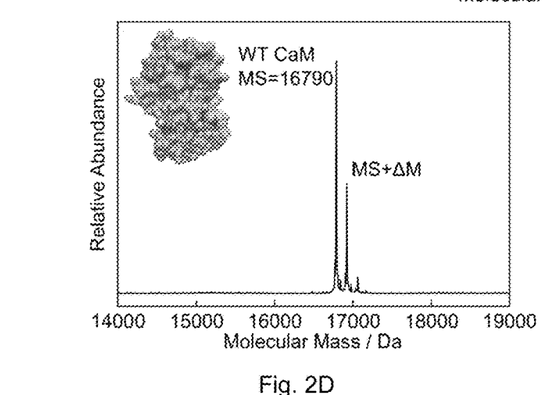
Figure 2E:
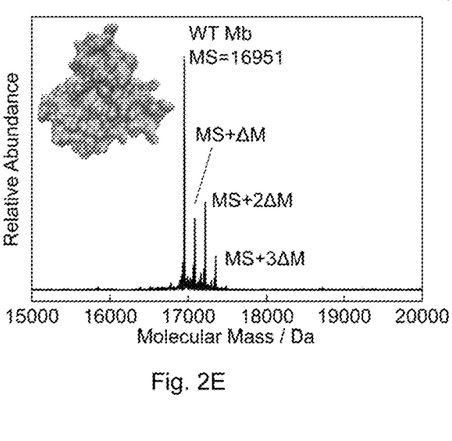
Figure 2F:
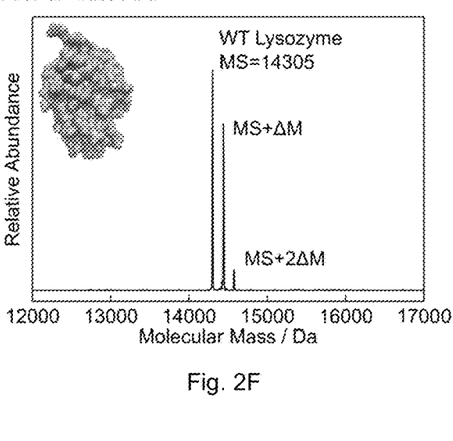

We then demonstrated that the TPAC bioconjugation method is amenable to labeling histidine residues on other proteins, including calmodulin, myoglobin and lysozyme. The yields vary for these proteins (FIGS. 2D-2F), and the reaction shows excellent histidine selectivity on calmodulin and myoglobin. Modest side-reactivity towards lysine is observed on lysozyme, but lysine labeling can be suppressed by lowering the pH to 7.5 to further block the nucleophilicity of the lysine residues by protonation, while increasing TPAC concentrations to compensate the decreased histidine reactivity. TPAC labeling in HeLa lysates also proceeds smoothly as shown by in-gel fluorescence and more importantly, pretreatments of lysates with competing electrophiles that block cysteine, lysine or serine residues do not affect the observed TPAC signal, suggesting that the reagent does not appreciably react with these competing amino acid residues. Taken together, the results show that TPAC is effective at selectively labeling native histidine residues on proteins.

Figure 3A:
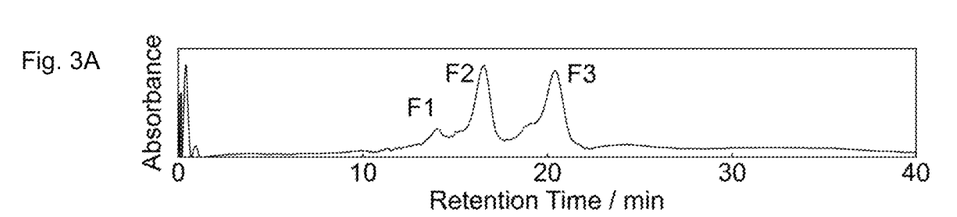
FIG. 3A: Chromatogram at 280 nm showing the separation of the reaction mixture between ribonuclease A and TPAC by strong cation exchange column. Three fractions, F1-3, were collected for analysis.
Figure 3B:
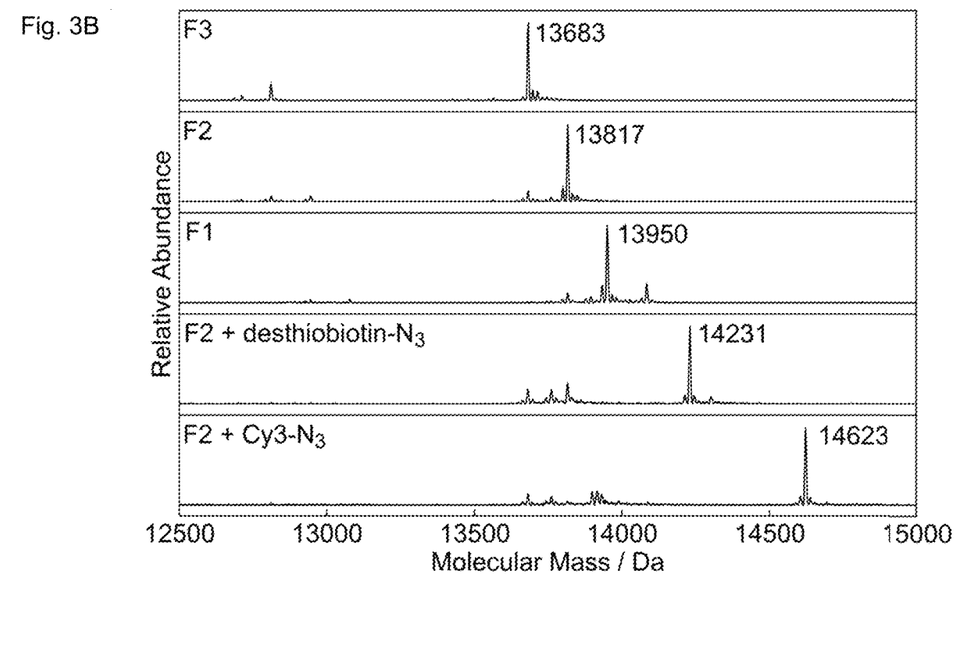
FIG. 3B: Deconvoluted mass spectra of ribonuclease A in F1-3, and TPAC-modified ribonuclease A in F2 reacted with the model azide compounds by CuAAC. Found masses are labelled next to the peak. Expected masses for non-, single- and double-labelled ribonuclease A are 13683, 13817, 13951 Da, respectively. Expected masses for single TPAC/desthiobiotin-$N_3$ and TPAC/Cy3-$N_3$ labelled ribonuclease A are 14231 and 14623 Da, respectively.

We then sought to apply this histidine bioconjugation method to install clickable payloads onto proteins. Considering that TPAC converts the slightly basic histidine residue into a rather acidic thiophosphoric acid derivative, we reasoned that the labeled protein can be separated readily from the unreacted protein by its charge difference. Indeed, the separation of the reaction mixture of ribonuclease A and TPAC is effective on a strong cation exchange column buffered at pH 4.2, giving rise to three fractions (FIG. 3A). The mass spectra of these fractions confirms our hypothesis: unreacted ribonuclease A carries more positive charge and elutes last, the doubly TPAC-modified ribonuclease A protein is less positively charged and elutes first, and the singly TPAC-modified protein elutes between these two fractions (FIG. 3B). After the facile isolation of TPAC-modified reaction products, we further performed copper(I)-catalyzed alkyne-azide cycloaddition (CuAAC) between mono-labeled ribonuclease A and either Cy3-$N_3$ or desthiobiotin-$N_3$ payloads for detection and enrichment, respectively (Table 2). As expected, the obtained protein is uniform with only one payload per protein molecule (FIG. 3B). Collectively, TPAC labeling with subsequent ion exchange chromatography and CuAAC chemistry provides a versatile and robust workflow to create homogenous proteins modified on histidine residues.

Figure 4A:
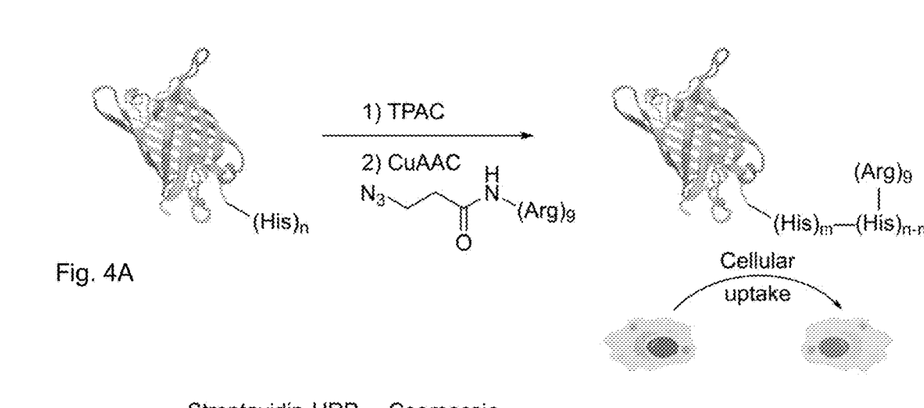
FIG. 4A: Scheme of bioconjugation of polyarginine onto His-tag of a fluorescent protein using TPAC.
Figure 4B:
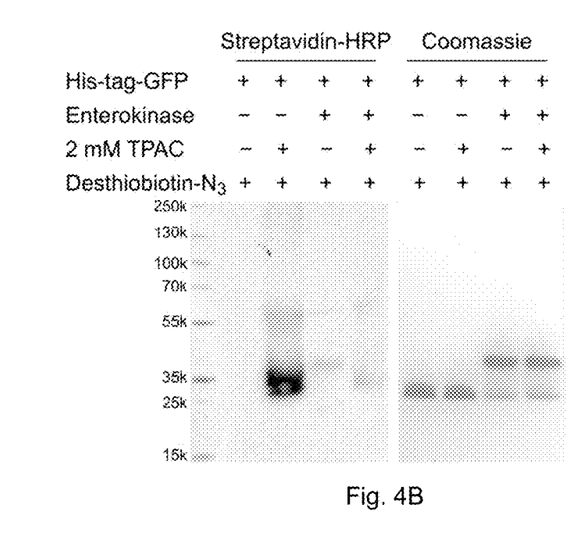
FIG. 4B: Streptavidin-HRP blot and coomassie stain showing that removal of the His-tag significantly reduces the labeling by TPAC. His-tagged GFP and native GFP prepared by enterokinase cleavage of His-tag were treated with TPAC, followed by CuAAC with desthiobiotin-$N_3$ and gel-analysis. Cleavage of His-tag leads to less coomassie staining but with similar migration on SDS-PAGE.
Figure 4C:
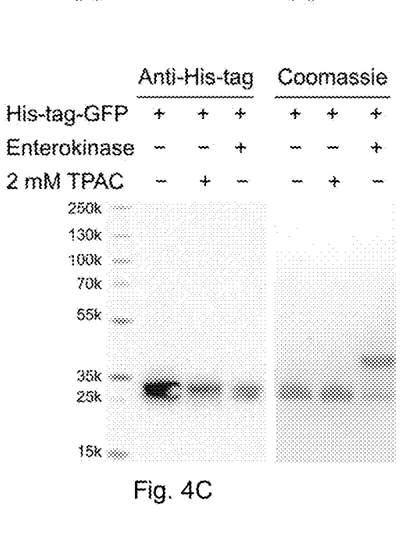
FIG. 4C: Western blot and coomassie stain showing that labelling of TPAC with His-tagged GFP significantly reduces its detection by His-tag antibody.
Figure 4D:
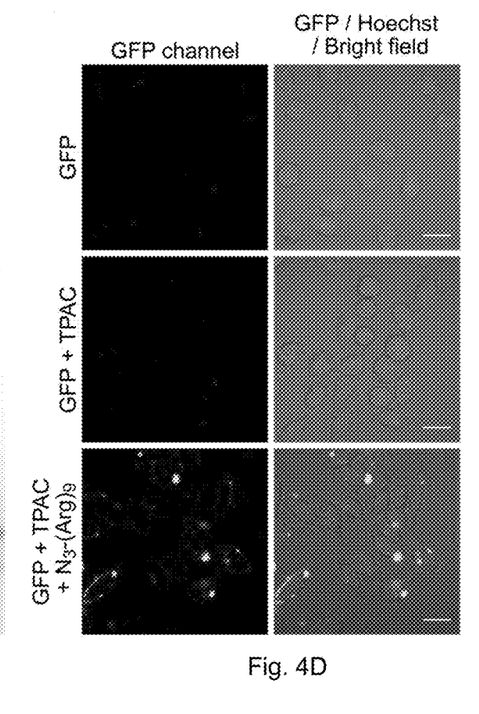
FIG. 4D: Transduction of functionalized GFP into live HeLa cells. Cells were incubated with GFP (0.1 µg/µL), stained with Hoechst 33342 and imaged. Scale-bars: 20 µm.

TPAC bioconjugation on His-tag for protein delivery. To showcase the potential merits of TPAC bioconjugation chemistry at the cellular level, we turned our attention to selective modification of polyhistidine-tagged proteins (e.g., His-tag). His-tag is a widely used method for purification of proteins by introducing a short polyhistidine peptide fused to the surface exposed portion of the protein of interest for sub-sequent resin capture and separation. We envisioned that this polyhistidine motif would greatly enhance the labeling efficiency of TPAC in a site-specific manner, and we demonstrated this possibility by combining TPAC labeling with further bioconjugation by CuAAC with polyarginine, a cell-penetrating peptide, to create a general method for enabling protein delivery into living cells (FIG. 4A). We utilized GFP bearing an N-terminal 10×His tag as a proof-of-concept protein, where TPAC-labeling greatly reduces binding and recognition of His-tag GFP by a His-tag antibody, consistent with efficient labeling of TPAC in this His-tag region (FIG. 4C). Indeed, TPAC labeling followed by CuAAC with desthiobiotin-$N_3$ on His-tag GFP produces a significantly stronger signal compared to GFP without the His-tag on a streptavidin blot (FIG. 4B), further indicating that TPAC selectively reacts with histidine residues on the His-tag rather than other histidine residues on this protein. Similarly, LC-MS analysis of the digested protein after TPAC treatment only identifies one to three modifications, all of which appear on the His-tag region. With this information in hand, we performed CuAAC between TPAC-labeled His-tag GFP and $N_3$-(Arg)$_9$-OH to introduce cell-penetrating capabilities onto the protein. Indeed, the (Arg)$_9$-functionalized GFP is now capable of being delivered into HeLa cells as shown by increases in intracellular green fluorescence as observed by confocal microscopy, whereas His-tagged GFP without TPAC or $N_3$-(Arg)$_9$-OH treatment results in no fluorescence signal over dark background (FIG. 4D). Similar results are also observed with an mCherry construct carrying an N-terminus 6×His-tag. Taken together, this line of experiments shows that TPAC provides covalent, histidine-selective bioconjugation that is functional in living cells.

This example discloses thiophosphorodichloridates inspired by native histidine phosphorylation processes as reagents for histidine-selective covalent modification of proteins. With TPAC, an alkyne-tagged version of this family of probes, we demonstrated efficient bioconjugation on model proteins with excellent selectivity for histidine over other potentially reactive amino acids. TPAC-labeled proteins are readily purified and can undergo further coupling with bioorthogonal click chemistry to introduce a variety of payloads. In one example to illustrate the utility of this approach, TPAC labeling was applied to introduce polyarginine motifs selectively onto His-tag proteins to endow membrane permeability and enable delivery into living cells. Owing to central importance of histidine residues in enzyme chemistry, this work provides a new type of reagent for probing histidine function in native contexts. Likewise, the efficient labeling of polyhistidine tags enables versatile protein functionalization for biochemical and protein engineering studies in both fundamental and applied settings. The methods maybe used in conjunction with selective methionine bioconjugation reagents that operate by redox-mediated nitrogen group transfer processes that inspired by native oxygen atom-transfer oxidations that transform methionine to methionine sulfoxide[22].

Experimental Section

Chemical and protein materials. All commercial reagents were used without further purification. Fmoc-Cys-OH was purchased from Chem-Impex (Wood Dale IL). All other Fmoc-protected amino acids were purchased from Ark Pharm (Arlington Heights IL). 2-(4-((bis((1-(tert-butyl)-1H-1,2,3-triazol-4-yl)methyl)amino)methyl)-1H-1,2,3-triazol-1-yl) acetic acid (BTTAA) was purchased from Click Chemistry Tools (Scottsdale AZ). Ribonuclease A from bovine pancreas, lyzome from chicken egg white, myoglobin from equine heart and all other chemicals were purchased from Sigma-Aldrich (St. Louis MO). Calmodulin, porcine was purchased from rPeptide (Watkinsville GA). His-tagged GFP was purchased from Sino Biological (Beijing, China). His-tagged mCherry was purchased from Origene (Rockville MD). Enterokinase was purchased from New England Biolabs (Ipswich MA). TEV protease was purchased from QB3 (San Francisco CA). Enzymes were used following the protocols provided by their manufacturer.

Reaction between phosphorus electrophiles and amino acids. Fmoc-protected amino acid was dissolved in DMSO (100 mM) and diluted to a final concentration of 0.5 mM in 25 mM HEPES buffer, pH 8.5 containing 20% MeCN unless otherwise noted. To this solution was added 5 mM of phosphorus electrophile (50× stock in MeCN). The reaction was performed at room temperature for 1 h unless otherwise noted, filtered and immediately subject to LC/MS analysis. For reaction with Fmoc-protected amino acid mixtures, 0.3 mM of each protected amino acid in 50 mM HEPES buffer, pH 8.5 containing 20% MeCN was reacted with 3 mM of TPAC.

Protein labelling with TPAC. Proteins were diluted into 25 mM HEPES, pH 8.5 to a concentration of 20 µM unless otherwise noted. Samples were labelled with 2 mM of TPAC (50× stock in MeCN). The reaction was performed at room temperature for 1 h. Samples were then subject to LC/MS analysis or further click reaction or LC-MS analysis.

Purification of TPAC-labelled ribonuclease A. The reaction mixture of RNase A with TPAC was diluted in 20 mM sodium succinate, pH 4.2 and was loaded onto HiTrap SP HP cation exchange chromatography column (1 mL, GE Healthcare, Chicago IL). The protein was then separated with a linear gradient from 20 mM sodium succinate, pH 4.2 to 25 mM succinate with 1 M NaCl, pH 4.2 at a flow rate of 1.0 mL/min over 40 min. The collected fractions were concentrated and buffer-exchanged into desired buffer for click reaction or LC/MS analysis.

Click reactions on TPAC-labelled proteins. We followed the protocol recommended by M. Finn, et al for click reactions.[46] Namely, protein solution in HEPES or PBS buffer was treated with 1 mM aminoguanidine hydrochloride (100× stock in water), 100 µM $CuSO_4$ (100× stock in water), 500 µM THPTA or BTTAA (100× stock in water), 100 µM organic azide (100× stock in DMSO or water) and 5 mM sodium ascorbate (100× stock in water). For reaction on his-tagged protein 100 µM $NiCl_2$ (100× stock in water) was also added. The reaction was mixed thoroughly and placed in the dark at room temperature. After 1 h the reaction was quenched by adding 500 µM EDTA.

For click reaction with Cy3-$N_3$, proteins were precipitated with acetone prior to click reaction to remove excess TPAC. The pellet was dissolved in PBS containing 0.1% SDS for click reaction, and precipitated again to remove unreacted dye. The pellet was then dissolved in running buffer and analyzed by SDS-PAGE.

For click reaction on TPAC-labelled, His-tagged proteins, proteins were buffer-exchanged into 25 mM HEPES, pH 7.5 by extensive ultrafiltration (Amnicon 10K, EMD Millipore, Hayward CA) prior to click reaction. After the click reaction, proteins were buffer-exchanged into PBS by extensive ultrafiltration to remove unwanted chemicals.

Cell culture and imaging Cells were grown in the Cell Culture Facility at the University of California, Berkeley. HeLa cells were cultured in DMEM supplemented with 10% FBS and glutamine (2 mM). One day before imaging, cells were passed and plated on eight-well chamber slides (Lab-Tek, Thermo Fisher).

For imaging, cells were grown on 8-well chamber slides (LabTek, Thermo Fisher) to desired confluency, washed with PBS and incubated with 0.1 mg/mL $(Arg)_9$-labelled GFP or mCherry in PBS for 15 min at 37° C. The cells were then washed with PBS and stained with 1 μM Hoechst 33342 for 15 min, washed again and imaged on a Zeiss LSM710 laser-scanning microscope with a 63× oil-immersion objective lens. Excitation was provided at 405 for Hoechst 33342, 488 nm for GFP and 543 nm for mCherry.

Synthesis of methyl propargyl thiophosphorochloridate (2). To a flask containing $PSCl_3$ (2 mL, 20 mmol) cooled in ice/water bath was added dry methanol (2.0 mL, 49 mmol) dropwise. The mixture was stirred for 15 min on ice and excess methanol was distilled under vacuum at the same temperature to give crude methyl thiophosphorodichloridate. Sodium (0.453 g, 19.7 mmol) was dissolved in cooled propargyl alcohol (6.0 mL, 104 mmol) to form an orange, thick solution, which was added dropwise to methyl thiophosphorodichloridate cooled in ice/water bath. The suspension was further stirred for 2 h at room temperature, diluted with $CH_2Cl_2$, filtered and purified by column chromatography (30:1 hexanes/EtOAc) to give product 2 as a colorless oil (2.4 g, 67%). $^1$H NMR (400 MHZ, $CDCl_3$) δ 4.85-4.80 (m, 2H), 3.91 (d, J=16.1 Hz, 3H), 2.63 (t, J=2.5 Hz, 1H). $^{13}$C NMR (101 MHZ, $CDCl_3$) δ 77.16, 76.45, 76.34, 56.92, 56.88, 56.01, 55.94. $^{31}$P NMR (162 MHZ, $CDCl_3$) δ 71.91. HRMS (APCI) m/z calcd 184.9587, found 184.9586 for $C_4H_7ClO_2PS^+$ $(M+H^+)$.

Synthesis of methyl propargyl thiophosphoramidate (1). Crude 2 in propargyl alcohol and $CH_2Cl_2$ was prepared as described above. Excess ammonia was led through this mixture to form $NH_4Cl$ as a precipitate. The mixture was filtered, concentrated and purified by column chromatography (2:1 hexanes/EtOAc) to give product 1 as a light yellow oil (2.1 g, 65% overall yield). $^1$H NMR (400 MHZ, MeOD) δ 4.62 (dd, J=10.5, 2.5 Hz, 2H), 3.68 (d, J=13.8 Hz, 3H), 2.94 (t, J=2.5 Hz, 1H). $^{13}$C NMR (101 MHZ, MeOD) δ 79.52, 79.41, 76.35, 55.05, 55.02, 53.75, 53.70. $^{31}$P NMR (162 MHz, MeOD) δ 78.25. HRMS (APCI) m/z calcd 166.0086, found 166.0097 for $C_4H_9NO_2PS^+$ $(M+H^+)$.

Synthesis of propargyl thiophosphorodichloridate (4, TPAC). To a solution of $PSCl_3$ (1.0 mL, 9.8 mmol) in $CH_2Cl_2$ (10 mL) was added propargyl alcohol (0.57 mL, 9.8 mmol) and $K_2CO_3$ (1.36 g, 9.8 mmol). After overnight stirring at room temperature, the mixture was filtered and purified by column chromatography (50:1 hexanes/EtOAc) to give product TPAC as a colorless oil with a pungent smell (1.1 g, 55%). $^1$H NMR (400 MHZ, $CDCl_3$) δ 4.94 (dd, J=15.9, 2.5 Hz, 2H), 2.72 (t, J=2.5 Hz, 1H). $^{13}$C NMR (101 MHZ, $CDCl_3$) δ 78.37, 75.53, 75.42, 58.56, 58.48. $^{31}$P NMR (162 MHZ, $CDCl_3$) δ 59.68. HRMS (APCI$^+$) m/z calcd 188.9092, found 188.9115 for $C_3H_4Cl_2OPS^+$ $(M+H^+)$.

Synthesis of propargyl phosphorodichloridate (5). $POCl_3$ (1.0 mL, 11 mmol) and propargyl alcohol (0.62 mL, 11 mmol) was dissolved in $Et_2O$ (20 mL) and cooled in dry ice/acetone bath under $N_2$. Triethylamine (1.5 mL, 11 mmol) was dissolved in $Et_2O$ (20 mL) and added dropwise via addition funnel to form a white suspension. The reaction mixture was warmed to room temperature and was furthered stirred at room temperature for 2 h. Trimethylamine hydrochloride was removed by filtration, and the solution was concentrated to give product 5 as a light yellow oil with a pungent smell (1.8 g, 99%). The product was used without further purification. $^1$H NMR (400 MHZ, $CDCl_3$) δ 4.92 (dd, J=14.5, 1.0 Hz, 2H), 2.76 (t, J=1.0 Hz 1H). $^1$H NMR (400 MHZ, $CDCl_3$) δ 4.94, 4.94, 4.90, 4.90, 3.48, 3.46, 2.76, 1.21, 1.19, 1.17. $^{13}$C NMR (101 MHZ, $CDCl_3$) δ 78.93, 74.96, 74.86, 58.56, 58.49. $^{31}$P NMR (162 MHz, $CDCl_3$) δ 8.70. LRMS (EI$^+$) m/z calcd 137.0, found 136.9 for $C_3H_3ClO_2P^+$ $(M-Cl^-)$.

Synthesis of methyl propargyl phosphorochloridate (3). Crude 5 with trimethylamine hydrochloride in $Et_2O$ was prepared as described above. The mixture was cooled again in dry ice/acetone bath. Dry methanol (0.43 mL, 11 mmol) and trimethylamine (1.5 mL, 11 mmol) in $Et_2O$ (20 mL) was added dropwise via addition funnel. The slurry was further stirred at room temperature for 3 h, filtered and concentrated to give product 3 as light yellow oil with a pungent smell (1.7 g, 93%). $^1$H NMR (400 MHZ, $CDCl_3$) δ 4.79 (dd, J=11.5, 2.5 Hz, 1H), 3.92 (d, J=13.8 Hz, 3H), 2.66 (t, J=2.5 Hz, 1H). $^{13}$C NMR (101 MHZ, $CDCl_3$) δ 78.92, 76.09, 76.00, 56.68, 56.63, 56.01, 55.94. $^{31}$P NMR (162 MHZ, $CDCl_3$) δ 6.74. HRMS (APCI$^+$) m/z calcd 168.9816, found 168.9855 for $C_4H_7ClO_3P^+$ $(M+H^+)$.

Synthesis of N-propargyl thiophosphoramidic dichloride (6). To a solution of $PSCl_3$ (0.30 mL, 2.9 mmol) in $CH_2Cl_2$ (5 mL) was added propargyl amine (0.19 mL, 2.9 mmol) and $K_2CO_3$ (0.41 g, 2.9 mmol). After 2 h stirring at room temperature, the mixture was filtered and purified by column chromatography (30:1 hexanes/EtOAc) to give product 6 as a yellow oil with a pungent smell (0.25 g, 49%). $^1$H NMR (400 MHZ, Acetone) δ 4.09 (dd, J=20.7, 2.5 Hz, 2H), 2.89 (t, J=2.5 Hz, 1H). $^{13}$C NMR (101 MHZ, Acetone) δ 79.94, 79.85, 74.13, 33.42. $^{31}$P NMR (162 MHz, Acetone) δ 57.59. HRMS (EI$^+$) m/z calcd 151.9, found 152.0 for $C_3H_4ClNPS^+$ $(M-Cl^-)$.

Synthesis of propargyl dithiophosphorodichloridate (7). S-propargyl thioacetate (0.35 mg, 3.1 mmol) was stirred with NaOH (0.16 g, 4.0 mmol) in MeOH (10 mL) under $N_2$ for 30 min. The mixture was then diluted with $CH_2Cl_2$ (30 mL), washed with $H_2O$ (×4) and dried $(Na_2SO_4)$. To this solution was added $PSCl_3$ (0.37 mL, 3.7 mmol) and $K_2CO_3$ (0.51 g, 3.7 mmol) and the mixture was stirred overnight. The mixture was filtered and purified by column chromatography (100:1 hexanes/EtOAc) to give product 7 as a light yellow oil, which degenerates into a solid mixture soon after concentration. $^1$H NMR (600 MHZ, $CDCl_3$) δ 3.75 (dd, J=15.6, 2.7 Hz, 2H), 2.35 (t, J=2.7 Hz, 1H).

Synthesis of 2-azidoethyl thiophosphorodichloridate 8. 2-Azidoethanol (0.43 g, 4.9 mmol) was dissolved in dry THF (15 mL) under $N_2$ and cooled in dry ice/acetone bath. To this solution was added dropwise nBuLi (2.0 mL, 2.5 M in hexanes) and stirred for 20 min at room temperature to form the lithium salt. To another flask cooled in dry ice/acetone bath was added THF (15 mL) and $PSCl_3$ (1.0 mL, 4.9 mmol) under $N_2$. The lithium salt solution was then added dropwise at this temperature and the mixture was then stirred for 1 h at room temperature. The mixture was concentrated, diluted in $CH_2Cl_2$, filtered to remove lithium chloride and purified by column chromatography (50:1 hexanes/EtOAc) to give product 8 as a light yellow oil with a pungent smell (0.60 g, 56%). $^1$H NMR (400 MHZ, $CDCl_3$) δ 4.45 (dt, J=11.0, 5.1 Hz, 2H), 3.63 (t, J=4.4 Hz, 2H). $^{13}$C NMR (101 MHz, $CDCl_3$) δ 69.62, 69.52, 50.16, 50.06. $^{31}$P NMR (162 MHz, $CDCl_3$) δ 59.05. HRMS (APCI$^+$) m/z calcd 191.9202, found 191.9219 for $C_2H_5Cl_2NOPS^+$ $(M-N_2+H^+)$.

Synthesis of (±)-3-butyn-2-yl thiophosphorodichloridate (9). (±)-3-Butyn-2-ol (0.77 mL, 9.8 mmol) was dissolved in dry THF (10 mL) under $N_2$ and cooled in dry ice/acetone bath. To this solution was added dropwise nBuLi (3.9 mL, 2.5 M in hexanes) and stirred for 20 min at room temperature to form the lithium salt. To another flask cooled in dry ice/acetone bath was added THF (20 mL) and $PSCl_3$ (1.0 mL, 9.8 mmol) under $N_2$. The lithium salt solution was then added dropwise at this temperature and the mixture was then stirred for 3h at room temperature. The mixture was concentrated, diluted in $CH_2Cl_2$, filtered to remove lithium chloride and purified by column chromatography (100:1 hexanes/EtOAc) to give product 9 as a colorless oil with a pungent smell (0.53 g, 26%). $^1$H NMR (400 MHZ, $CDCl_3$) δ 5.46 (dqd, J=13.3, 6.6, 2.1 Hz, 1H), 2.71 (d, J=2.2 Hz, 1H), 1.71 (dd, J=6.6, 0.8 Hz, 3H). $^{13}$C NMR (101 MHZ, $CDCl_3$) δ 79.99, 79.92, 76.64, 69.25, 69.16, 23.21, 23.14. $^{31}$P NMR (162 MHZ, $CDCl_3$) δ 58.98. HRMS (APCI$^+$) m/z calcd 202.9249, found 202.9261 for $C_4H_6Cl_2OPS^+$ (M+H$^+$).

Scheme 1 Different routes for synthesis of phosphorus electrophiles.

Scheme 2 Reaction yields of phosphorus electrophiles on Fmoc-His-OH.$^a$ $^a$Conditions: 0.5 mM Fmoc-His-OH, 5 mM electrophile, 25 mM HEPES pH 8.5, 20% MeCN, 1h; yields were determined by HPLC. $^b$Reactant readily degenerates and forms precipitate.

REFERENCES (1) Stephanopoulos, N.; Francis, M. B. Choosing an Effective Protein Bioconjugation Strategy. Nat. Chem. Biol. 2011, 7 (12), 876-884.
(2) Spicer, C. D.; Davis, B. G. Selective Chemical Protein Modification. Nat. Commun. 2014, 5, 4740.
(3) Mckay, C. S.; Finn, M. G. Click Chemistry in Complex Mixtures: Bioorthogonal Bioconjugation. Chem. Biol. 2014, 21 (9), 1075-1101.
(4) Koniev, O.; Wagner, A. Developments and Recent Advancements in the Field of Endogenous Amino Acid Selective Bond Forming Reactions for Bioconjugation. Chem. Soc. Rev. 2015, 44 (15), 5495-5551.
(5) Boutureira, O.; Bernardes, G. J. L. Advances in Chemical Protein Modification. Chem. Rev. 2015, 115 (5), 2174-2195.
(6) Vinogradova, E. V.; Zhang, C.; Spokoyny, A. M.; Pentelute, B. L.; Buchwald, S. L. Organometallic Palladium Reagents for Cysteine Bioconjugation. Nature 2015, 526 (7575), 687-691.
(7) Zhang, C.; Welborn, M.; Zhu, T.; Yang, N. J.; Santos, M. S.; Voorhis, T. V.; Pentelute, B. L. π-Clamp-Mediated Cysteine Conjugation. Nat. Chem. 2016, 8 (2), 120-128.
(8) Willwacher, J.; Raj, R.; Mohammed, S.; Davis, B. G. Selective Metal-Site-Guided Arylation of Proteins. J. Am. Chem. Soc. 2016, 138 (28), 8678-8681.
(9) Messina, M. S.; Stauber, J. M.; Waddington, M. A.; Rheingold, A. L.; Maynard, H. D.; Spokoyny, A. M. Organometallic Gold (III) Reagents for Cysteine Arylation. J. Am. Chem. Soc. 2018, 140 (23), 7065-7069.

(10) Matos, M. J.; et al. Chemo- and Regioselective Lysine Modification on Native Proteins. J. Am. Chem. Soc. 2018, 140 (11), 4004-4017.

(11) Ward, C. C.; Kleinman, J. I.; Nomura, D. K. NHS-Esters As Versatile Reactivity-Based Probes for Mapping Proteome-Wide Ligandable Hotspots. ACS Chem. Biol. 2017, 12 (6), 1478-1483.

(12) Hacker, S. M.; Backus, K. M.; Lazear, M. R.; Forli, S.; Correia, B. E.; Cravatt, B. F. Global Profiling of Lysine Reactivity and Ligandability in the Human Proteome. Nat. Chem. 2017, 9 (12), 1181-1190.

(13) Liu, Y.; Patricelli, M. P.; Cravatt, B. F. Activity-Based Protein Profiling: The Serine Hydrolases. Proc. Natl. Acad. Sci. 1999, 96 (26), 14694-14699.

(14) Kidd, D.; Liu, Y.; Cravatt, B. F. Profiling Serine Hydrolase Activities in Complex Proteomes. Biochemistry (Mosc.) 2001, 40 (13), 4005-4015.

(15) McGrath, N. A.; Andersen, K. A.; Davis, A. K. F.; Lomax, J. E.; Raines, R. T. Diazo Compounds for the Bioreversible Esterification of Proteins. Chem. Sci. 2014, 6 (1), 752-755.

(16) deGruyter, J. N.; Malins, L. R.; Baran, P. S. Residue-Specific Peptide Modification: A Chemist's Guide. Biochemistry (Mosc.) 2017, 56 (30), 3863-3873.

(17) Schlick, T. L.; Ding, Z.; Kovacs, E. W.; Francis, M. B. Dual-Surface Modification of the Tobacco Mosaic Virus. J. Am. Chem. Soc. 2005, 127 (11), 3718-3723.

(18) Romanini, D. W.; Francis, M. B. Attachment of Peptide Building Blocks to Proteins Through Tyrosine Bioconjugation. Bioconjug. Chem. 2008, 19 (1), 153-157.

(19) Ban, H.; Gavrilyuk, J.; Barbas, C. F. Tyrosine Bioconjugation through Aqueous Ene-Type Reactions: A Click-Like Reaction for Tyrosine. J. Am. Chem. Soc. 2010, 132 (5), 1523-1525.

(20) Antos, J. M.; Francis, M. B. Selective Tryptophan Modification with Rhodium Carbenoids in Aqueous Solution. J. Am. Chem. Soc. 2004, 126 (33), 10256-10257.

(21) Antos, J. M.; McFarland, J. M.; Iavarone, A. T.; Francis, M. B. Chemoselective Tryptophan Labeling with Rhodium Carbenoids at Mild PH. J. Am. Chem. Soc. 2009, 131 (17), 6301-6308.

(22) Lin, S.; Yang, X.; Jia, S.; Weeks, A. M.; Hornsby, M.; Lee, P. S.; Nichiporuk, R. V.; Iavarone, A. T.; Wells, J. A.; Toste, F. D.; et al. Redox-Based Reagents for Chemoselective Methionine Bioconjugation. Science 2017, 355 (6325), 597-602.

(23) Gutteridge, A.; Thornton, J. M. Understanding Nature's Catalytic Toolkit. Trends Biochem. Sci. 2005, 30 (11), 622-629.

(24) Dokmanić, I.; Šikić, M.; Tomić, S. Metals in Proteins: Correlation between the Metal-Ion Type, Coordination Number and the Amino-Acid Residues Involved in the Coordination. Acta Crystallogr. D Biol. Crystallogr. 2008, 64 (3), 257-263.

(25) Ohata, J.; Minus, M. B.; Abernathy, M. E.; Ball, Z. T. Histidine-Directed Arylation/Alkenylation of Backbone N—H Bonds Mediated by Copper(II). J. Am. Chem. Soc. 2016, 138 (24), 7472-7475.

(26) Ohata, J.; Zeng, Y.; Segatori, L.; Ball, Z. T. A Naturally Encoded Dipeptide Handle for Bioorthogonal Chan-Lam Coupling. Angew. Chem. Int. Ed. 2018, 57 (15), 4015-4019.

(27) Waibel, R.; et al. Stable One-Step Technetium-99m Labeling of His-Tagged Recombinant Proteins with a Novel Tc(I)-carbonyl Complex. Nat. Biotechnol. 1999, 17 (9), 897-901.

(28) Kapanidis, A. N.; Ebright, Y. W.; Ebright, R. H. Site-Specific Incorporation of Fluorescent Probes into Protein: Hexahistidine-Tag-Mediated Fluorescent Labeling with (Ni2+: Nitrilotriacetic Acid)N-Fluorochrome Conjugates. J. Am. Chem. Soc. 2001, 123 (48), 12123-12125.

(29) Lata, S.; Gavutis, M.; Tampé, R.; Piehler, J. Specific and Stable Fluorescence Labeling of Histidine-Tagged Proteins for Dissecting Multi-Protein Complex Formation. J. Am. Chem. Soc. 2006, 128 (7), 2365-2372.

(30) Wang, X.; Jia, J.; Huang, Z.; Zhou, M.; Fei, H. Luminescent Peptide Labeling Based on a Histidine-Binding Iridium(III) Complex for Cell Penetration and Intracellular Targeting Studies. Chem.—Eur. J. 2011, 17 (29), 8028-8032.

(31) Lai, Y.-T.; Chang, Y.-Y.; Hu, L.; Yang, Y.; Chao, A.; Du, Z.-Y.; Tanner, J. A.; Chye, M.-L.; Qian, C.; Ng, K.-M.; et al. Rapid Labeling of Intracellular His-Tagged Proteins in Living Cells. Proc. Natl. Acad. Sci. 2015, 112 (10), 2948-2953.

(32) Li, X.; Ma, H.; Dong, S.; Duan, X.; Liang, S. Selective Labeling of Histidine by a Designed Fluorescein-Based Probe. Talanta 2004, 62 (2), 367-371.

(33) Li, X.; Ma, H.; Nie, L.; Sun, M.; Xiong, S. A Novel Fluorescent Probe for Selective Labeling of Histidine. Anal. Chim. Acta 2004, 515 (2), 255-260.

(34) Takaoka, Y.; Tsutsumi, H.; Kasagi, N.; Nakata, E.; Hamachi, I. One-Pot and Sequential Organic Chemistry on an Enzyme Surface to Tether a Fluorescent Probe at the Proximity of the Active Site with Restoring Enzyme Activity. J. Am. Chem. Soc. 2006, 128 (10), 3273-3280.

(35) Wakabayashi, H.; Miyagawa, M.; Koshi, Y.; Takaoka, Y.; Tsukiji, S.; Hamachi, I. Affinity-Labeling-Based Introduction of a Reactive Handle for Natural Protein Modification. Chem.—Asian J. 3 (7), 1134-1139.

(36) Puttick, J.; Baker, E. N.; Delbaere, L. T. J. Histidine Phosphorylation in Biological Systems. Biochim. Biophys. Acta BBA-Proteins Proteomics 2008, 1784 (1), 100-105.

(37) Besant, P. G.; Attwood, P. V. Detection and Analysis of Protein Histidine Phosphorylation. Mol. Cell. Biochem. 2009, 329 (1-2), 93-106.

(38) Kee, J.-M.; Muir, T. W. Chasing Phosphohistidine, an Elusive Sibling in the Phosphoamino Acid Family. ACS Chem. Biol. 2012, 7 (1), 44-51.

(39) Potel, C. M.; Lin, M.-H.; Heck, A. J. R.; Lemeer, S. Widespread Bacterial Protein Histidine Phosphorylation Revealed by Mass Spectrometry-Based Proteomics. Nat. Methods 2018, 15 (3), 187-190.

(40) Medzihradszky, K. F.; et al. Synthesis and Characterization of Histidine-Phosphorylated Peptides. Protein Sci. 6 (7), 1405-1411.

(41) Hohenester, U. M.; Ludwig, K.; König, S. Chemical Phosphorylation of Histidine Residues in Proteins Using Potassium Phosphoramidate—a Tool for the Analysis of Acid-Labile Phosphorylation. Curr. Drug Deliv. 2013, 10 (1), 58-63.

(42) Lasker, M.; et al. Protein Histidine Phosphorylation: Increased Stability of Thiophosphohistidine. Protein Sci. 8 (10), 2177-2185.

(43) Pirrung, M. C.; James, K. D.; Rana, V. S. Thiophosphorylation of Histidine. J. Org. Chem. 2000, 65 (25), 8448-8453.

(44) Ruman, T.; et a. Thiophosphorylation of Free Amino Acids and Enzyme Protein by Thiophosphoramidate Ions. Bioorganic Chem. 2010, 38 (2), 74-80.

(45) Westheimer, F. H. Why Nature Chose Phosphates. Science 1987, 235 (4793), 1173-1178.

(46) Hong, V.; Presolski, S. I.; Ma, C.; Finn, M. G. Analysis and Optimization of Copper-Catalyzed Azide-Alkyne Cycloaddition for Bioconjugation. Angew. Chem. Int. Ed. 48 (52), 9879-9883.

Supplement

Table 1 Stability of TPAC-labelled Fmoc-His-OH Purified TPAC-labelled Fmoc-His-OH (0.5 mM) was treated under the following conditions in water (1-7) or PBS (8-12) and analyzed by HPLC after indicated period of time.

| Entry | Additive (concentration) | Temperature/° C. | Time/h | Hydrolysis ratio |
|---|---|---|---|---|
| 1 | Formic acid (1M) | 25 | 1 | 1% |
| 2 | Formic acid (1M) | 25 | 14 | 15% |
| 3 | HCl (0.2M) | 25 | 1 | <1% |
| 4 | HCl (0.2M) | 25 | 14 | 20 |
| 5 | $NH_3 \cdot H_2O$ (1M) | 25 | 1 | <1% |
| 6 | $NH_3 \cdot H_2O$ (1M) | 25 | 14 | <1% |
| 7 | NaOH (0.2M) | 25 | 1 | n.d.[a] |
| 8 | PBS | 80 | 1 | 2% |
| 9 | PBS | 80 | 14 | 32% |
| 10 | TCEP (5 mM)[b] | 65 | 0.5 | <1% |
| 11 | Dithiothreitol (5 mM) | 65 | 0.5 | 1% |
| 12 | Iodoacetamide (10 mM) | 37 | 1 | 2% |

[a] Fmoc protection group was cleaved during treatment.
[b] Tris(2-carboxyethyl)phosphine.

Table 2 Structure and molecular weight of model azide compounds: $Cy3-N_3$ and $desthiobiotin-N_3$.

Cy3-N₃
Molecular weight: 806.2

Desthiobiotin-N₃
Molecular weight: 414.3

Analysis Methods

Reactions on protected amino acid were analyzed by LC/MS using 1220 Infinity LC (Agilent, Santa Clara CA) coupled with Expression-L Compact Mass Spectrometer (Advion, Ithaca NY). Reaction mixtures with single protected amino acid were separated on a Zorbax rapid resolution cartridge (Agilent). Mixtures with multiple protected amino acids were separated on a Zorbax SB-phenyl column (Agilent, 4.6×250 mm, 5 µm). Solvent A was water+0.05% formic acid and solvent B was methanol+0.05% formic acid. The linear gradient employed for single protected amino acid was 25-100% B in 6.5 min and 100% B for 1.5 min; for multiple amino acids mixture was 45-100% B in 30 min and 100% B for 10 min.

Intact protein samples were analyzed using a Synapt G2-Si mass spectrometer equipped with an ionKey ESI source (Protein ionKey, C4, 1.7 µm, 0.150×50 mm, 300 Å), operated in the positive ion mode, and connected in line with an Acquity M-class LC system (Waters, Milford MA). This instrumentation is located in the QB3/Chemistry Mass Spectrometry Facility at the University of California, Berkeley. The obtained mass spectra were deconvoluted using UniDec.[1]

Proteolytically digested protein samples were analyzed using an LTQ-Orbitrap-XL mass spectrometer equipped with an electrospray ionization (ESI) source, operated in the positive ion mode, and connected in line with an UltiMate3000 RSLCnano liquid chromatography (LC) system (Thermo Fisher). The LC system was equipped with a reversed-phase analytical column (Acclaim PepMap100, C18, 3 µm, 0.075×250 mm, 100 Å, Thermo Fisher). The obtained data were processed with Trans-Proteomic Pipeline using the Comet search algorism (Institute for Systems Biology, Seattle WA).[2] The MS2 spectra were annotated with a mass tolerance of 15 ppm. The extracted-ion chromatograms (XIC) of MS1 were generated from the .ms1 file from RawConverter, using an in-house script that picks correctly-charged precursor ions with a mass tolerance of 20 ppm.

Enzymatic Digestion of TPAC-Labelled Protein for LC-MS/MS Analysis

Protein (0.5 mg/mL) was labelled with 2 mM TPAC following the general procedure unless otherwise noted. Labelled protein was precipitated by acetone to remove excess TPAC. The pellet was dissolved in 25 mM HEPES, pH 8.0 containing 6 M urea and subject to reduction (TCEP, 5 mM, 20 min) and alkylation (iodoacetamide, 10 mM, 40 min at 37° C.). Protein was precipitated again by acetone, suspended in 25 mM HEPES, pH 8.0 and digested by trypsin (1:20, Promega, Madison WI) overnight at 37° C.

Synthesis of Phosphorus Electrophiles and Related Chemicals

All reactions utilizing air- or moisture-sensitive reagents were performed in dried glassware under an atmosphere of dry $N_2$. THF used for anhydrous reactions was dried and stored over 4 Å molecular sieves. 2-Azidoethanol[3] and succinimidyl 3-azidopropanoate[4] were synthesized according to literature procedure. 3-Azidopropanoic acid was purchased from Click Chemistry Tools. H-(Arg)$_9$-OH trifluoroacetate salt was purchased from Bachem (Bubendorf, Switzerland). All other reagents were purchased from Sigma-Aldrich. $^1$H NMR, $^{13}$C NMR and $^{31}$P NMR spectra were collected in CDCl$_3$, MeOD or acetone (Cambridge Isotope Laboratories, Cambridge MA) at 25° C. on AVB-400, AVQ-400 or AV-600 spectrometers at the College of Chemistry NMR Facility at UC Berkeley. All chemical shifts in $^1$H NMR and $^{13}$C NMR are reported in the standard & notation of ppm relative to residual solvent peak (CDCl$_3$ δH=7.26, δC=77.16; MeOD δH=3.31, δC=49.00; acetone: δH=2.05, δC=29.84), and for $^{31}$P NMR 85% phosphoric acid in sealed capillary tube is used as internal standard (δP=0.00). Splitting patterns are indicated as follows: s, singlet; d, doublet; t, triplet; q, quartet; m, multiplet; br, broad. Low resolution election ionization mass spectral analysis was carried out using Agilent 5975C 7890A GC/MS System. High resolution mass spectral analysis (ESI-MS and APCI-MS) were carried out at LBNL Catalysis Facility at the Lawrence Berkeley National Laboratory (Berkeley Lab) using PerkinElmer AxION® 2 TOF MS.

3-Azidoacetyl-(Arg)$_9$-OH. H-(Arg)$_9$-OH trifluoroacetate salt (1 mg, approx. 0.5 µmol) was dissolved in 400 µL H$_2$O in an Eppendorf tube. To this solution was added HEPES buffer (100 µL, 50 mM pH=7.5) and succinimidyl 3-azidopropanoate (2.54 mg, 12 µmol) in DMSO (500 µL). The solution was mixed thoroughly and reacted in the dark for 3 h. The solution was then loaded onto a strong cation exchange spin column (Thermo Fisher). The column was washed with 25 mM ammonium acetate (2×400 µL) and eluted with 2 M ammonium acetate. The eluent was concentrated in a vacuum chamber overnight, and the residue was dissolved in water to a final volume of 50 µL to give an approx. 10 mM stock solution. HRMS (ESI$^+$) m/z calcd 507.6567, found 507.6502 for $C_{57}H_{116}N_{39}O_{11}{}^{3+}$ (M+3H$^+$); calcd 514.9840, found 514.9745 for $C_{57}H_{115}N_{39}NaO_{11}{}^{3+}$ (M+2H$^+$+Na$^+$).

Potassium O-propargyl (N$^2$-Fmoc-L-histidino)thiophosphate. Fmoc-His-OH (0.20 g, 0.53 mmol) and K$_2$CO$_3$ (1.1 g, 8.0 mmol) was dissolved in 4:6 H$_2$O/MeCN (15 mL). To this mixture was added TPAC (0.30 g, 1.6 mmol) in MeCN (5 mL) over 1 h under vigorous stirring. The mixture was further stirred for 2 h and the desired product was separated by RP-HPLC to give the product as an off-white solid (0.22 g, 75%). $^1$H NMR (400 MHZ, MeOD) δ 8.87 (s, 1H), 7.78 (d, J=7.4 Hz, 2H), 7.63 (d, J=7.2 Hz, 2H), 7.49 (s, 1H), 7.34 (dt, J=28.2, 7.3 Hz, 4H), 4.68-4.58 (m, 2H), 4.51 (dd, J=9.3, 4.8 Hz, 1H), 4.37-4.28 (m, 2H), 4.20 (t, J=6.7 Hz, 1H), 3.27 (d, J=4.7 Hz, 1H), 3.09 (dd, J=15.1, 9.7 Hz, 1H), 2.76-2.66 (m, 1H). $^{31}$P NMR (162 MHz, MeOD) δ 49.01. HRMS (ESI$^+$) m/z calcd 512.1040, found 512.1092 for $C_{24}H_{23}N_3O_6PS^+$ (M+H$^+$).

REFERENCES (1) Marty, M. T.; et al. Deconvolution of Mass and Ion Mobility Spectra: From Binary Interactions to Polydisperse Ensembles. Anal. Chem. 2015, 87 (8), 4370-4376.
(2) Eng, J. K.; Jahan, T. A.; Hoopmann, M. R. Comet: An Open-Source MS/MS Sequence Database Search Tool. PROTEOMICS 13 (1), 22-24.
(3) Hounsou, C.; et al. Time-Resolved FRET Binding Assay to Investigate Hetero-Oligomer Binding Properties: Proof of Concept with Dopamine D1/D3 Heterodimer. ACS Chem. Biol. 2015, 10 (2), 466-474.
(4) Grandjean, C.; Boutonnier, A.; Guerreiro, C.; Fournier, J.-M.; Mulard, L. A. On the Preparation of Carbohydrate-Protein Conjugates Using the Traceless Staudinger Ligation. J. Org. Chem. 2005, 70 (18), 7123-7132.

The invention claimed is:

1. A method of labeling a protein comprising:
Reacting the protein with a thiophosphorodichloridate reagent under conditions to effect chemoselective histidine conjugation and form a resultant conjugate of the protein and the thiophosphorodichloridate reagent;
wherein the thiophosphorodichloridate reagent is selected form the group consisting of:

and

2. The method of claim 1 further comprising reacting the resultant conjugate with a payload, wherein said payload comprises a complementary azide or alkyne functional group to the thiophosphorodichloridate reagent.

3. The method of claim 2 wherein the reacting is via chemistry selected from the group consisting of: copper-assisted alkyne-azide cycloaddition (CuAAC) chemistry, and strain-promoted alkyne-azide cycloaddition (SPAAC).

4. The method of claim 3 wherein the reagent is thiophosphoro alkyne dichloridate (TPAC) having the structure:

5. The method of claim 2 wherein the payload is a small molecule pharmaceutical, a DNA, an RNA, a lipid, a sugar, a polypeptide, a protein, or a detectable label.

6. The method of claim 2 wherein the conjugate is of general formula:

wherein R1 is the protein, R2 is the payload, and L is the resultant linker from the alkyne azide cycloaddition reaction.

7. The method of claim 1 wherein the protein comprises a polyhistidine tag and the method effects covalent modification of the tag.

8. The method of claim 2 wherein the protein comprises a polyhistidine tag and the method effects covalent modification of the tag.

9. The method of claim 3 wherein the protein comprises a polyhistidine tag and the method effects covalent modification of the tag.

10. The method of claim 6 wherein the protein comprises a polyhistidine tag and the method effects covalent modification of the tag.

11. The method of claim 1 wherein the conjugation is bioconjugation, wherein the protein is labeled inside a living cell.

12. The method of claim 2 wherein the conjugation is bioconjugation, wherein the protein is labeled inside a living cell.

13. The method of claim 3 wherein the conjugation is bioconjugation, wherein the protein is labeled inside a living cell.

14. The method of claim 6 wherein the conjugation is bioconjugation, wherein the protein is labeled inside a living cell.

15. The method of claim 1, wherein the reagent is thiophosphoro alkyne dichloridate (TPAC) of structure: